United States Patent [19]

Liu et al.

[11] 4,305,870

[45] Dec. 15, 1981

[54] INTRAVENOUS PLASMA DERIVATIVES AND THEIR PRODUCTION

[75] Inventors: Daniel T. H. Liu; Annita L. S. Weidenbach; Rong-chang Pai, all of Troy, Mich.

[73] Assignee: Immuno Aktiengesellschaft für chemisch-medizinische Produkte, Vienna, Austria

[21] Appl. No.: 159,079

[22] Filed: Jun. 13, 1980

Related U.S. Application Data

[63] Continuation of Ser. No. 7,855, Jan. 31, 1979, abandoned.

[51] Int. Cl.³ ................................................. C07G 7/00
[52] U.S. Cl. ................................. 260/112 B; 424/101
[58] Field of Search ...................... 260/112 B; 424/101

[56] References Cited

U.S. PATENT DOCUMENTS

| | | | |
|---|---|---|---|
| 3,083,194 | 3/1963 | Thies et al. | 260/112 B |
| 3,449,316 | 6/1969 | Querry | 260/112 B |
| 3,466,368 | 9/1969 | Sela et al. | 260/112 B X |
| 3,664,994 | 5/1972 | Perper | 260/112 B |
| 3,674,863 | 7/1972 | Fisher et al. | 424/92 |
| 3,869,436 | 3/1975 | Falksveden | 260/112 B |
| 4,100,149 | 7/1978 | Meiller et al. | 260/112 B X |
| 4,136,094 | 1/1979 | Condie | 260/112 B X |

OTHER PUBLICATIONS

Alving et al., New England J. Med. 299, 66–70 (1978).

*Primary Examiner*—Howard E. Schain
*Attorney, Agent, or Firm*—Brumbaugh, Graves, Donohue & Raymond

[57] ABSTRACT

Intravenous plasma derivatives having an acceptably lowered content of externally caused deleterious activity or exogenous activity, and their method of production are provided. The method includes the steps of mixing bentonite and an aqueous solution of plasma derivative containing exogenous activity, the bentonite and the mixing time being sufficient to adsorb exogenous activity, and isolating the aqueous phase from the bentonite. Optionally, for the removal of residual exogenous activity, the step of treatment of the aqueous phase with bentonite is repeated and/or the bentonite-treated aqueous phase is further purified by ion-exchange chromatography.

6 Claims, No Drawings

INTRAVENOUS PLASMA DERIVATIVES AND THEIR PRODUCTION

This is a continuation of application Ser. No. 7,855, filed Jan. 31, 1979, now abandoned.

SUMMARY AND DETAILED DESCRIPTION

The present invention relates to plasma derivatives for intravenous use having an acceptably lowered content of exogenous activity and to a method for their production.

In conventional practice, plasma derivatives made by the Cohn cold alcohol fractionation method are known to contain undesirable, deleterious exogenous activity such as prekallikrein activator (PKA) activity, activated clotting factor, and esterase activity. The plasma derivatives, notably immune globulins, which contain too much exogenous activity are unsuitable for intravenous administration. Some plasma protein fraction (PPF) preparations have been reported on intravenous administration to cause hypotensive reaction in patients; the above-mentioned PKA activity has been identified as the exogenous activity causing hypotension (Alving et al., New England J. Med. 299: 66–70, 1978, incorporated herein by reference).

According to the present invention, plasma derivatives for intravenous administration are produced by a method comprising mixing bentonite and an aqueous solution of plasma derivative containing exogenous activity including PKA activity, activated clotting factor, and/or esterase activity, the quantity of bentonite and the mixing time being sufficient to adsorb from at least about the major part of the contained exogenous activity to about substantially all of said exogenous activity; and isolating the resulting aqueous phase from the bentonite, whereby an aqueous solution of plasma derivative is obtained having an acceptably lowered content of exogenous activity. The term "exogenous activity" used herein is intended to mean PKA activity, activated clotting factor, and/or esterase activity. The term "alcohol fractionated immune globulin" used herein is intended to mean immune globulin produced by fractionation methods following or based on the Cohn cold alcohol extraction method described in J.A.C.S. 68: 459 et seq., 1946 (which description is incorporated herein by reference) and elsewhere. The term "plasma derivative" used herein is intended to mean immune globulin, plasma protein fraction (PPF), albumin, antihemophilic factor (AHF), prothrombin factor or factor IX concentrate, and other like fractions derived from plasma. The term "immune globulin" used herein is intended to mean any of various normal immune or hyperimmune globulins known in the art, especially human globulins such as immune human serum globulin, Rho(D) immune human globulin, pseudomonas immune human globulin, vaccinia immune human globulin, pertussis immune human globulin, and the like.

For purposes of the invention, the quantities, temperatures and times involved in the mixing step are subject to considerable variation. The plasma derivative is used as an aqueous solution preferably obtained by solubilizing the respective plasma derivative as a powder in a buffer such as 0.02 M sodium acetate buffer, pH 7.0, or by diluting a concentrated buffered aqueous solution of the plasma derivative with the same buffer. For the purpose, preferred concentrations of the plasma derivative solution are in the range from about 5 to about 16% (w/v). The amount of exogenous activity removed by adsorption on bentonite is proportional to the amount of bentonite used. For example, bentonite in the amount of about 20 to about 30 mg for each ml. of 5–16% plasma derivative solution removes substantially all exogenous activity from the plasma derivative solution.

Bentonite used for the invention has the properties of montmorillonite and is available in various forms. Montmorillonite has the approximate chemical formula $[(Al,Fe)_{1.67}Mg_{0.33}]Si_4O_{10}(OH)_2(Na,Ca_{0.33})$. A preferred bentonite is a volcanic clay material which has the following typical analysis and particle size distribution:

PARTICLE SIZE

When dispersed in water, separating into extremely fine particles, as follows:
- 96% to 97% finer than 44 microns (No. 325 Standard U.S. Sieve)
- 93% to 94% finer than 5 microns
- 87% to 89% finer than 0.5 micron
- 60% to 65% finer than 0.1 micron

| CHEMICAL ANALYSIS, MOISTURE FREE BASIS | | |
|---|---|---|
| | PERCENT BY WT. (VARIES BETWEEN) | |
| Silica ($SiO_2$) | 58.0 | 64.0 |
| Alumina ($Al_2O_3$) | 18.0 | 21.0 |
| Ferric Oxide ($Fe_2O_3$) | 2.5 | 2.8 |
| Magnesia (MgO) | 2.5 | 3.2 |
| Lime (CaO) | 0.1 | 1.0 |
| Soda ($Na_2O$) | 1.5 | 2.7 |
| Potash ($K_2O$) | 0.2 | 0.4 |
| Ferrous Oxide (FeO) | 0.2 | 0.4 |
| Titanium Oxide ($TiO_2$) | 0.1 | 0.2 |
| Other minor constituents | 0.5 | 0.8 |
| Chemically-held water ($H_2O$) | | 5.64 |
| Mechanically-held water ($H_2O$) | | 0.00 |

More preferably, one uses a commercially available small particle bentonite supplied under the name of VOLCLAY$^{tm}$, grade BC-USP, by American Colloid Company, Skokie, Ill. This material has a dry sieve analysis of 99% finer than 10 microns (1500 sieve) and an average wet sieve analysis of 96% finer than 0.5 microns.

The desired adsorption in a preferred embodiment takes place by adding or incorporating the bentonite with the plasma derivative solution, mixing at room temperature, at which temperature the adsorption takes place within about 30 minutes. The supernatant or first aqueous phase of the resulting mixture is then isolated conveniently by centrifuging, e.g. at 12000Xg. in the cold (10° C.) for about 30 minutes. The precipitate is washed with buffer (e.g., 0.02 M acetate buffer, pH 7 or other suitable buffer) and diluted to about 7 to 8% (w/v) protein concentration. The wash procedure is carried out by resuspending the precipitate by mixing and then centrifuging (e.g., at 12,000 Xg for 30 minutes at 10° C.). The resulting spernatant or second aqueous phase is added to the previously isolated first aqueous phase. The resulting pooled aqueous phase contains relatively little exogenous activity. If desired, it can be finished in any suitable way for administration purposes. For example, it can be finished to contain about 5% protein in 0.3 M glycine 0.2% NaCl solution at pH 6.8±0.2 and sterile filtered using AP25, PH and GS Millipore$^{tm}$ filters.

The amount of exogenous activity, if any, remaining after a single bentonite treatment is small. It can be removed by adsorption according to a further feature of the invention, by a repeated bentonite treatment or by ion exchange chromatography which preferably may be done by treatment with an anion exchange adsorbent for exogenous activity, preferably, for example, by batchwise diethylaminoethyl (DEAE)—cellulose treatment. Bentonite is particularly effective in removing esterase activity while DEAE—cellulose is especially effective in removing PKA activity. For best results, a combination of single treatments first with bentonite and then with DEAE—cellulose is used to remove the exogenous activity. Advantageously, the antibody content is substantially completely unaffected by such treatments.

The invention is illustrated by the following example which is a preferred embodiment.

A dilute (8–16%,w/v) solution of pseudomonas immune globulin, derived from Cohn cold alcohol fractionated plasma (U.S. Pat. No. 3,674,863, incorporated herewith by reference), is prepared by solubilizing pseudomonas immune globulin powder in 0.02 M sodium acetate buffer, pH 7.0 or by diluting 16% (w/v) pseudomonas immune globulin solution with the same buffer. Bentonite (Volclay, BC-USP, American Colloid Co.) 20–30 mg/ml is added either dry or as a wet precipitate. It if is added wet, it is first resuspended in 0.02 M sodium acetate buffer, pH 7 or in distilled water 30 minutes prior to use and then centrifuged at 12,000 xg, 30 minutes at 10° C. The bentonite is added with stirring to the globulin (8–16%) solution. The mixture is stirred for 30 minutes at room temperature and then centrifuged at 12,000 xg, 10° C. for 30 minutes. The supernatant is decanted off and saved. The precipitate is washed with enough 0.02 M acetate buffer, pH 7, to dilute the final product to approximately 7–8% (w/v) protein concentration. The wash procedure is carried out by resuspending the precipitate by mixing and then centrifuging at 12,000 xg, 10° C., 20 minutes and adding the supernatant to the previously decanted globulin solution. At this point, most of esterase activity and PKA activity should be removed. If some PKA activity remains, it may be removed by repeating the above-described absorption on bentonite and recovery or by treatment with an anion exchange adsorbent and isolation of purified globulin. The latter treatment is done by first stirring the solution for one hour at 4° C. with diethylaminoethyl ether of cellulose (known in the art as DEAE-cellulose; DE-52, Whatman Co.) equilibrated previously with 0.02 M acetate buffer, pH 7 at a ratio of 1:2 to 1:4 (wet weight in grams of DEAE-cellulose ml. of globulin solution). The mixture is then filtered with suction using a sintered glass funnel or centrifuged to separate the DEAE-cellulose. The DEAE-cellulose is washed with enough 0.02 M acetate, pH 7, to produce a final 5% protein solution and is made to contain 0.3 M glycine and 0.2% by weight NaCl. Adjust pH to 6.8±0.2. The final purified pseudomonas immune globulin product, sterile filtered using AP25, pH and GS Millipore filters, can be used as it is for intravenous injection.

The pseudomonas globulin product produced has a lowered content of exogenous activity as seen from the following tables showing typical results obtained by treatment with bentonite either once (Table 1) or twice (Table 2) or by a combination treatment first with bentonite and then with DEAE-cellulose (Table 3), all as compared with untreated (control) globulin. The assays used are known in the art: prekallikrein activator, N$^\alpha$-tosyl-L-arginine[$^3$H]methylester (TAME) method, Alving et al., N. Eng. J. Med., 299:66–70, 1978; prekallikrein activator, benzoyl arginyl ethyl ester (BAEE) method, proceedings of the Workshop in Measurement of Potentially Hypotensive Agents, Bureau of Biologics, FDA, Bethesda, Md., September, 1977; partial thromboplastin time (PTT), Kingdon et al., Thrombos. Diathes, Haemorrh (Stuttg.), 1975, 33, 617.

TABLE 1

PSEUDOMONAS IMMUNE GLOBULIN TREATED WITH BENTONITE

|  | CONTROL | BENTONITE TREATMENT |
|---|---|---|
| Volume (ML) | 25 | 24 |
| Total Protein (MG) | 2085 | 1526 |
| Recovery (%) | 100 | 73.2 |
| PKA-BAEE (MU/ML) | 595 | 56 |
| Percent Original | 100 | 9.4 |
| Esterase - BAEE ($\Delta$ OD253 × 10$^{-2}$) | 7.5 | 0.6 |
| Percent Original | 100 | 8 |
| PTT Ratio* | 0.14 | 0.47 |
| Total Antibody | 22275 | 26352 |
| Recovery (%) | 100 | 100 |
| PKA - TAME | 2800 | 300 |
| Percent Original | 100 | 11 |
| Esterase - TAME | 100 | 18 |

*Partial thromboplastin time of sample divided by PTT of TRIS buffer.

These results show that the exogenous activity of the globulin product is reduced to about 9% (PKA-BAEE), 8% (esterase-BAEE), 11% (PKA-TAME), and 18% (esterase-TAME). Also, the partial thromboplastin time ratio (a measure of clotting time) is desirably increased to 0.47.

TABLE 2

PSEUDOMONAS IMMUNE GLOBULIN TREATED WITH BENTONITE TWICE

|  | CONTROL | BENTONITE ONCE | BENTONITE TWICE |
|---|---|---|---|
| Volume (ML) | 40 | 38 | 38 |
| Total Protein (MG) | 3264 | 2166 | 954 |
| Recovery (%) | 100 | 66.4 | 29.2 |
| PKA-BAEE (MU/ML) | 379 | 85 | 0 |
| Percent Original | 100 | 22 | 0 |
| Esterase ($\Delta$ OD 253 × 10$^{-3}$) | 9 | 0 | 0 |
| PTT Ratio | 0.15 | 0.44 | 0.86 |
| Total Antibody | 35640 | 41724 | 19456 |
| Recovery | 100 | 100 | 55 |

These results show that treatment of pseudomonas immune globulin with bentonite according to the invention favorably reduces the exogenous activity. In particular, PKA activity is reduced 22% by a single treatment and 100% by two treatments. Esterase is eliminated, and the partial thromboplastin time ratio is desirably increased to 0.44 and 0.86. The antibody content is comprised only by the second bentonite treatment.

TABLE 3
PSEUDOMONAS IMMUNE GLOBULIN TREATED WITH BENTONITE AND DEAE - CELLULOSE

| | CONTROL | BENTONITE TREATED | BENTONITE AND DEAE - CELLULOSE | |
| --- | --- | --- | --- | --- |
| | | | (1:3) | (1:2) |
| Volume (ML) | 40 | 38 | 54.3 | 51.6 |
| Total Protein (MG) | 3264 | 2166 | 2085 | 1858 |
| Percent Recovery | 100 | 66.4 | 63.9 | 56.9 |
| PKA-BAEE (MU/ML) | 379 | 85 | 0 | 0 |
| Percent Original | 100 | 22 | 0 | 0 |
| Esterase-BAEE ($\Delta$ OD253 $\times$ 10$^{-3}$) | 9 | 0 | 0 | 0 |
| PTT Ratio | 0.15 | 0.44 | 0.57 | 0.55 |
| Total Antibody | 35640 | 41724 | 36707 | 34882 |
| Recovery (%) | 100 | 100 | 100 | 98 |

These results show that treatment of pseudomonas immune globulin according to the invention, first with bentonite and them with DEAE-cellulose (one part by weight to either 3 or 2 parts by volume of globulin solution) favorably reduces the exogenous activity; PKA activity and esterase are both reduced to zero. The partial thromboplastin time ratio is favorably increased to about 0.55. Also, the antibody content is substantially the same as that of the control globulin.

We claim:

1. A method of producing a plasma derivative selected from the group consisting of immune globulin, plasma protein fraction (PPF), albumin, antihemophilic factor (AHF), prothrombin factor and factor IX concentrate, for intravenous administration, consisting of:
    (a) mixing bentonite and an aqueous solution of an alcohol fractionated plasma derivative, containing exogenous activity including PKA activity, activated clotting factor, and/or esterase activity, the quantity of bentonite and the mixing time being sufficient to adsorb from at least about the major part of the contained exogenous activity to about substantially all of said exogenous activity
    (b) separating the aqueous phase from the bentonite with adsorbed exogenous activity
    (c) subjecting said aqueous phase obtained to treatment with an anion exchange adsorbent, and
    (d) separating the resulting purified aqueous solution of plasma derivatives from said adsorbent.

2. A method according to claim 1, comprising subjecting the purified solution obtained in step (d) to repeated mixing with bentonite.

3. A method of producing immune globulin for intravenous administration, consisting of:
    (a) mixing 20 to 30 mg bentonite per ml of 5 to 16% aqueous solution of alcohol fractionated immune globulin, containing exogenous activity including PKA activity, activated clotting factor, and/or esterase activity, for about 30 min.
    (b) separating the aqueous phase from the bentonite with adsorbed exogenous activity
    (c) subjecting said aqueous phase obtained to treatment with an anion exchange adsorbent, containing DEAE, and
    (d) separating the resulting purified aqueous solution of immune globulin from said adsorbent.

4. A method according to claim 3, comprising subjecting the purified solution obtained in step (d) to repeated mixing with bentonite.

5. A method of producing a pseudomonas immune globulin product for intravenous administration, consisting of:
    (a) preparing a dilute solution of pseudomonas immune globulin from Cohn cold alcohol fractionated plasma
    (b) adding bentonite to the solutin of pseudomonas immune globulin with stirring
    (c) separating the aqueous phase from the bentonite
    (d) subjecting said aqueous phase obtained to a treatment with DEAE-cellulose and
    (e) separating the resulting purified aqueous solution of pseudomas immune globulin from said DEAE-cellulose.

6. A method according to claim 5, comprising subjecting the purified solution obtained in step (e) to repeated mixing with bentonite.

* * * * *

UNITED STATES PATENT AND TRADEMARK OFFICE
CERTIFICATE OF CORRECTION

PATENT NO. : 4,305,870
DATED : Dec. 15, 1981
INVENTOR(S) : Liu et al.

It is certified that error appears in the above—identified patent and that said Letters Patent is hereby corrected as shown below:

Col. 2, line 60, "spernatant" should read --supernatant--. Col. 3, line 30, "It if" should read --If it--; lines 47-48, "absorption" should read --adsorption--. Col. 4, line 27, "$10^{-2}$" should read --$10^{-3}$--; line 68, "comprised" should read --compromised--. Col. 5, line 23, "them" should read --then--. Col. 6, line 41, "solutin" should read --solution--; line 47, "pseudomas" should read --pseudomonas--.

Signed and Sealed this

Seventeenth Day of August 1982

[SEAL]

Attest:

Attesting Officer

GERALD J. MOSSINGHOFF
Commissioner of Patents and Trademarks